(12) United States Patent
Cassidy (10) Patent No.: US 7,865,072 B2
(45) Date of Patent: Jan. 4, 2011

(54) INTRAVENOUS FLUID WARMING SYSTEM (75) Inventor: David E. Cassidy, Chelmsford, MA (US)

(73) Assignee: General Electric Company, Schenectady, NY (US)

( * ) Notice: Subject to any disclaimer, the term of this patent is extended or adjusted under 35 U.S.C. 154(b) by 1149 days.

(21) Appl. No.: 11/385,085

(22) Filed: Mar. 21, 2006

(65) Prior Publication Data

US 2006/0222350 A1  Oct. 5, 2006

Related U.S. Application Data (60) Provisional application No. 60/663,857, filed on Mar. 21, 2005.

(51) Int. Cl.
*A61F 7/00* (2006.01)
(52) U.S. Cl. ........................ 392/470; 604/113
(58) Field of Classification Search ................. 392/470; 604/113
See application file for complete search history.

(56) References Cited

U.S. PATENT DOCUMENTS

| | | | | |
|---|---|---|---|---|
| 3,443,060 A * | 5/1969 | Smith | ........................ | 392/470 |
| 3,590,215 A * | 6/1971 | Anderson et al. | ........... | 392/470 |
| 4,019,020 A * | 4/1977 | Bilbee et al. | ................ | 392/470 |
| 4,293,762 A * | 10/1981 | Ogawa | ....................... | 392/470 |
| 4,464,563 A * | 8/1984 | Jewett | ........................ | 392/470 |
| 4,680,445 A * | 7/1987 | Ogawa | ....................... | 392/470 |
| 4,906,816 A * | 3/1990 | van Leerdam | .............. | 392/470 |
| 5,250,032 A * | 10/1993 | Carter et al. | ................ | 604/113 |
| 5,319,170 A | 6/1994 | Cassidy | ....................... | 219/630 |
| 5,420,962 A * | 5/1995 | Bakke | ........................ | 392/470 |
| 6,047,108 A * | 4/2000 | Sword et al. | ................ | 392/470 |
| 6,096,007 A * | 8/2000 | Haan et al. | .................. | 604/147 |
| 6,336,003 B1 * | 1/2002 | Mitsunaga et al. | .......... | 392/470 |
| 6,480,257 B2 | 11/2002 | Cassidy et al. | .............. | 352/470 |
| 6,535,689 B2 | 3/2003 | Augustine et al. | ........... | 392/470 |
| 6,643,454 B1 * | 11/2003 | Rochelle | ...................... | 392/485 |
| 6,722,782 B2 * | 4/2004 | Faries et al. | ................. | 374/162 |
| 6,788,885 B2 * | 9/2004 | Mitsunaga et al. | .......... | 392/470 |
| 7,289,724 B2 * | 10/2007 | Furnrohr et al. | ............. | 392/470 |
| 2002/0081109 A1 * | 6/2002 | Mitsunaga et al. | .......... | 392/470 |
| 2002/0181948 A1 * | 12/2002 | Akahane | ..................... | 392/470 |
| 2004/0190885 A1 * | 9/2004 | Entenman et al. | ........... | 392/470 |
| 2005/0008354 A1 | 1/2005 | Cassidy | | |
| 2006/0153549 A1 * | 7/2006 | Cazzini et al. | .............. | 392/470 |

* cited by examiner

*Primary Examiner*—Thor S Campbell
(74) *Attorney, Agent, or Firm*—Alan Taboada; Moser IP Law Group (57) ABSTRACT

A fluid warming device includes axially or longitudinally slidable covers that retain a removable heat exchange body in a housing in heat exchange communication with a heater assembly while allowing flow through the heat exchange body to be observed. In another aspect, a fluid warming system increases or decreases power to a heater assembly to adjust the fluid temperature to ensure that the fluid is at an appropriate temperature when it reaches the patient.

16 Claims, 10 Drawing Sheets

INTRAVENOUS FLUID WARMING SYSTEM

CROSS REFERENCE TO RELATED APPLICATIONS

This application claims the benefit under 35 U.S.C. §119 (e) of U.S. Provisional Application No. 60/663,857, filed on Mar. 21, 2005, the disclosure of which is incorporated by reference herein.

STATEMENT REGARDING FEDERALLY SPONSORED RESEARCH OR DEVELOPMENT

N/A

BACKGROUND OF THE INVENTION

Intravenous (IV) fluid warming devices are known that heat an IV fluid prior to introducing the fluid into a patient. Warmed IV fluids that are administered at very low flow rates can cool as they flow down the IV tubing to the patient. Often this heat loss is ignored. One prior art approach has been to simply heat the fluid to 41° C. to try to overcome the loss for all flow rates.

In another aspect of fluid warming, most IV fluid warmers heat fluid through flexible plastic walls. Because these walls are inefficient in transferring heat, heaters are exposed to both sides of the disposable set. This requires inserting the disposable set into a slot or hinged clam shell configuration. Both of these designs do not allow the user to see the fluid passing through the heat exchanger. As these plastic walls are flexible, the pressure necessary for good heat transfer cannot be guaranteed as it is supplied only by the gravitational force of the IV fluid bag height. Cleaning of configurations with slots is difficult and typically requires special tools or even disassembly, such as in the case of blood spills.

One type of exemplary medical fluid warming system is described in US 2005-0008354. In this device, fluid passes along a generally serpentine fluid flow path through a removable/disposable heat exchange body. The heat exchange body is in thermal contact with a resistive film heater via thermally conductive layers interposed between the heat exchange body and the heater. Temperature sensors are provided that sense the temperature of the heat exchange body and of the heater.

SUMMARY OF THE INVENTION

In one aspect of the present invention, a fluid warming system includes a pair of sliding covers that maintains a removable heat exchange body in place in heat exchange communication with a heater assembly. The heat exchange body is pressed in place by the covers in the closed position to guarantee good thermal conductivity. Fluid passing through the heat exchange body remains visible to the user. The heat exchange body is easily inserted and removed by sliding the covers to a open position. The moving covers can double as user input mechanisms by turning the power on and off and muting alarms. The covers do not cover any indicators present on the heat exchange body. The covers can be readily removed for cleaning, and the covers can be used as a mounting mechanism.

In another aspect of the present invention, power to the heater can be increased or decreased to adjust the fluid temperature to ensure that the fluid is at an appropriate temperature when it reaches the patient.

DESCRIPTION OF THE DRAWINGS

The invention will be more fully understood from the following detailed description taken in conjunction with the accompanying drawings in which.

DETAILED DESCRIPTION OF THE INVENTION

A fluid warming device 10 according to the present invention is illustrated in FIGS. 1-7. The fluid warming device includes a housing 12 having a main body 14 and two sliding covers 16. Within the housing, supported by the main body, are a removable heat exchange body 18 and a heater assembly 20. The sliding covers are independently slidable to a closed position in which they retain the removable heat exchange body in place, as described more fully below. The slidable covers are preferably identical.

Figure 7:
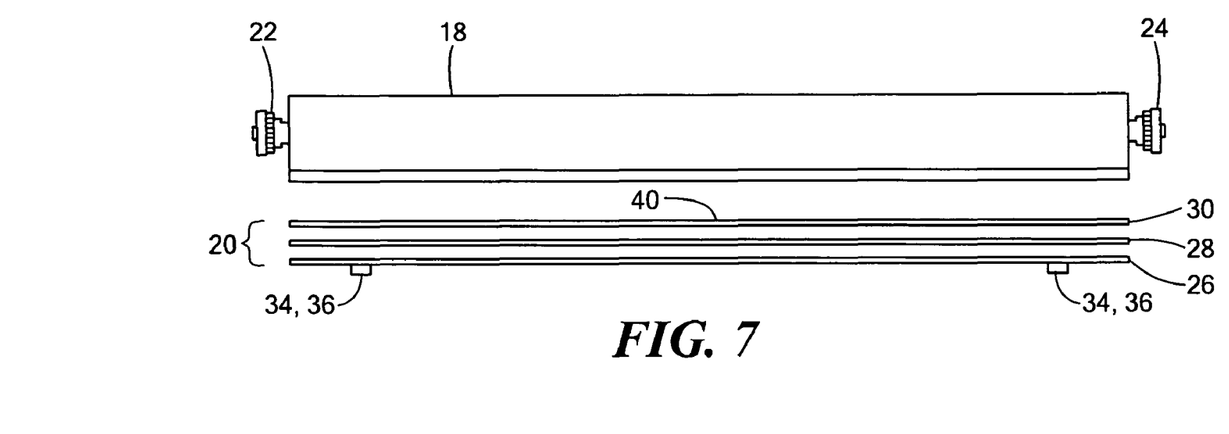
FIG. 7 is a schematic view of a disposable set and heater assembly of the fluid warming device of FIG. 1.

The removable heat exchange body 18 and the heating assembly 20 are illustrated schematically in FIG. 7. The heat exchange body, also called a disposable or removable set, includes an input port 22 connectable to an IV tubing line from a source of IV fluid, which may include an infusion pump. The disposable set also includes an output port 24 connectable to a further IV tubing line to deliver the IV fluid to the patient. Within the disposable set, the IV fluid flows along a flow path (not shown) having a serpentine or other suitable configuration between the input and output ports to optimize heat transfer to the fluid. See, for example, US Patent Pub. No. 2005-0008354, the disclosure of which is incorporated by reference herein. The disposable set is formed from any suitable material, such as aluminum, to facilitate heat transfer to the fluid flowing therein. When inserted in the housing with the sliding covers in a closed position, the disposable set is held in thermal contact with the heater assembly, so that heat transfer from the heater assembly to the disposable set causes heating of an IV fluid flowing therethrough.

The heater assembly 20 is affixed within the main body 14 of the housing 12. The heater assembly includes a heater 26 and one or more thermally conductive layers 28, 30 interposed between the disposable set and the heater. Preferably, the heater is an electrically powered resistive thin film heater. A power line 32 to the heater from a suitable power source is provided. Alternatively, the device may include a battery compartment or a connection to a battery pack, for example, for portable operation. Temperature sensors 34, 36 are provided that sense the temperature of the disposable set and of the heater. See, for example, US Patent Pub. No. 2005-0008354. The thermally conductive layers also electrically insulate the disposable set from the resistive heater. One thermally conductive layer 28 may suitably comprise a phase transition material, and the other thermally conductive layer 30 may suitably comprise a material such as a graphite to optimize heat transfer between the heater and the disposable set. See, for example, US Patent Pub. No. 2005-0008354. It will be appreciated that other or further thermally conductive layers may be provided. The main body 14 includes a compartment 38 on one side to receive the disposable set 18 in contact with an exposed surface 40 of the uppermost thermally conductive layer 30.

As noted above, the heat exchange body or disposable or disposable set 18 is removable from the housing. The disposable set can be removed from the main body of the housing by sliding the two opposed sliding covers outwardly in opposite directions. In this manner, the removable set can be lifted out of the housing with the IV tubing still attached to the input and output connectors, without breaking the fluid path. Finger cutouts 42 may be provided for ease of grasping the disposable set in the main body.

Any suitable sliding mechanism to allow the covers to move axially into the closed position can be provided. In the embodiment shown, the main body 14 of the housing includes protruding longitudinal tracks 46 along two opposed longitudinal outer wall surfaces of the main body. See FIG. 5. The sliding covers include complementary longitudinal recesses 48 along inner wall surfaces that mate with the tracks and allow the covers to slide axially along the main body. When in the closed position, the sliding covers extend over the edges of the disposable set within the recess of the main body, thereby retaining the disposable set therein. See FIG. 1. The covers also compress the disposable set to the outermost thermally conducting surface 40 of the heater assembly. This compression provides the necessary pressure for proper heat transfer between the heater assembly and the disposable set. Preferably, the covers are retained in the closed position by frictional engagement with the disposable set Alternatively, any suitable latching or retaining mechanism may be provided.

Also, the covers 16 do not block the view of the bulk of the mid portion of the disposable set 18, allowing the operator to view the fluid passing through the disposable set. The disposable set is also keyed to the main body 14 in any suitable manner so that it fits within the compartment in the correct orientation. For example, one end 47 of the disposable set may be rounded to fit within an correspondingly rounded portion 49 of the compartment 38. The disposable set may include an arrow 50 thereon to provide an indication of the direction of flow, so that the disposable set is inserted in the housing in the correct orientation. The covers do not block this arrow. Also, the main body preferably includes indicator lights, such as LEDs, thereon. For example, one LED 52 may provide an indication of temperature at the output port, and another LED 54 may provide an indication that the heater is connected to the power source. The covers do not block these indicator lights either.

In one embodiment, the covers 16 can be maintained in two positions on the main body or can be removed fully from the main body. While on the main body, the covers can be in a fully closed position or an open position. The covers can include magnets or Hall Effect devices or other proximity sensors that interface with a corresponding component within the main body to determine the positions of the covers and cause operation of any appropriate switches. In a further embodiment, the covers can be maintained in a third or intermediate, half closed, position on the main body, described further below.

More particularly, in the fully closed position, (see FIG. 1), the covers 16 apply full pressure to the disposable set 18 to ensure good thermal contact with the heater assembly. In this position, the sliding covers can also be used to turn the power on to commence warming and/or to activate any audible or visible alarm(s). In the half closed position (see FIG. 2), the disposable set is still held in place by the covers, but warming is stopped, the audible alarm is silenced, and the visual indicators are turned off. The status LED could be flashed in battery operation to inform the user that the warmer is connected to the battery and draining. When the covers are in the open position (see FIG. 3), the disposable set 18 can be inserted and removed. No heating takes place, the audible alarm is silenced, and visual indicators are turned off. The status LED could be flashed in battery operation to inform the user that the heater is connected to the battery and draining.

Figure 1:
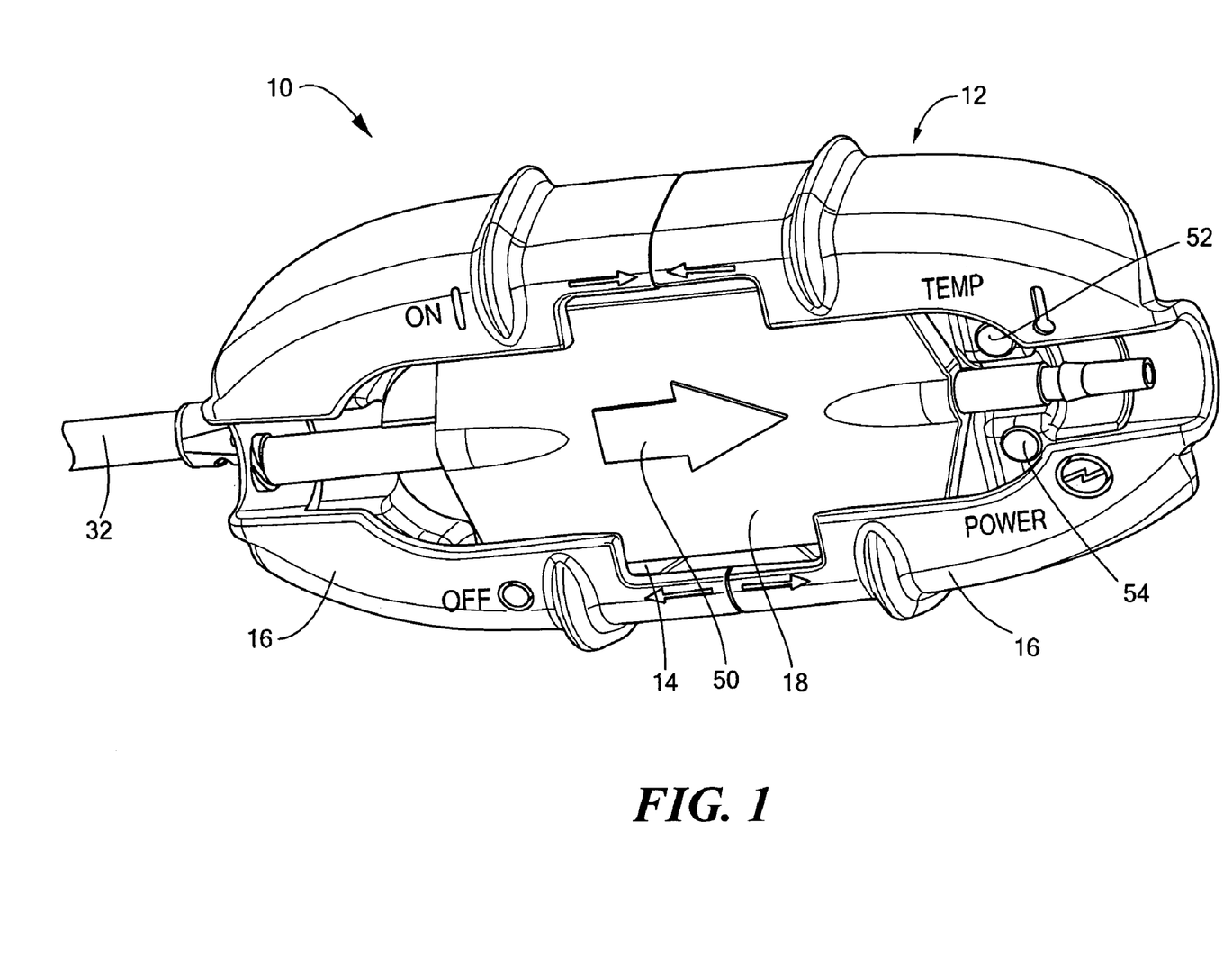
FIG. 1 is an isometric view of a fluid warming device illustrating slidable covers in a closed position according to the present invention.
Figure 2:
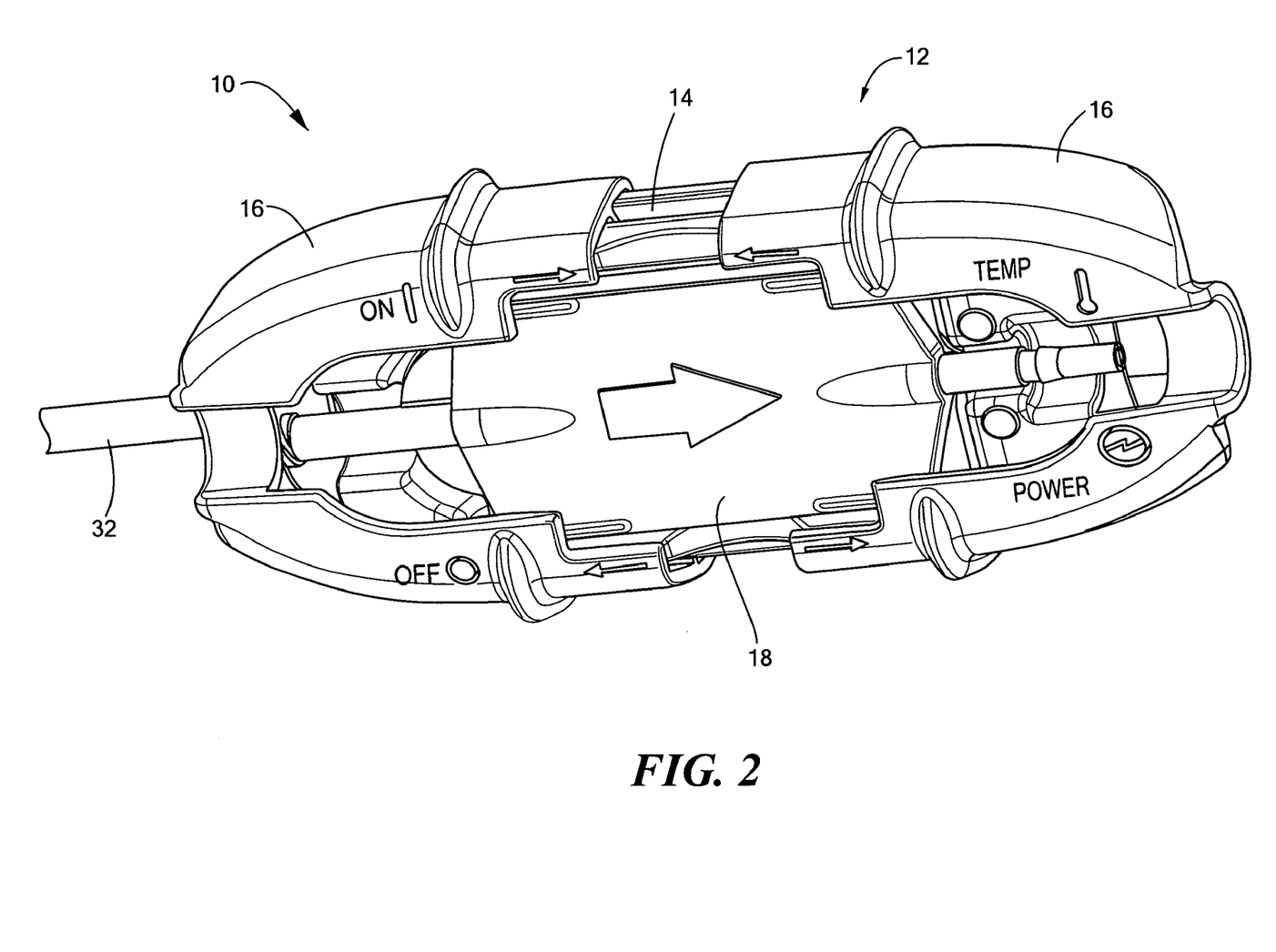
FIG. 2 is an isometric view of the fluid warming device of FIG. 1 illustrating the slidable covers in a half closed position.
Figure 3:
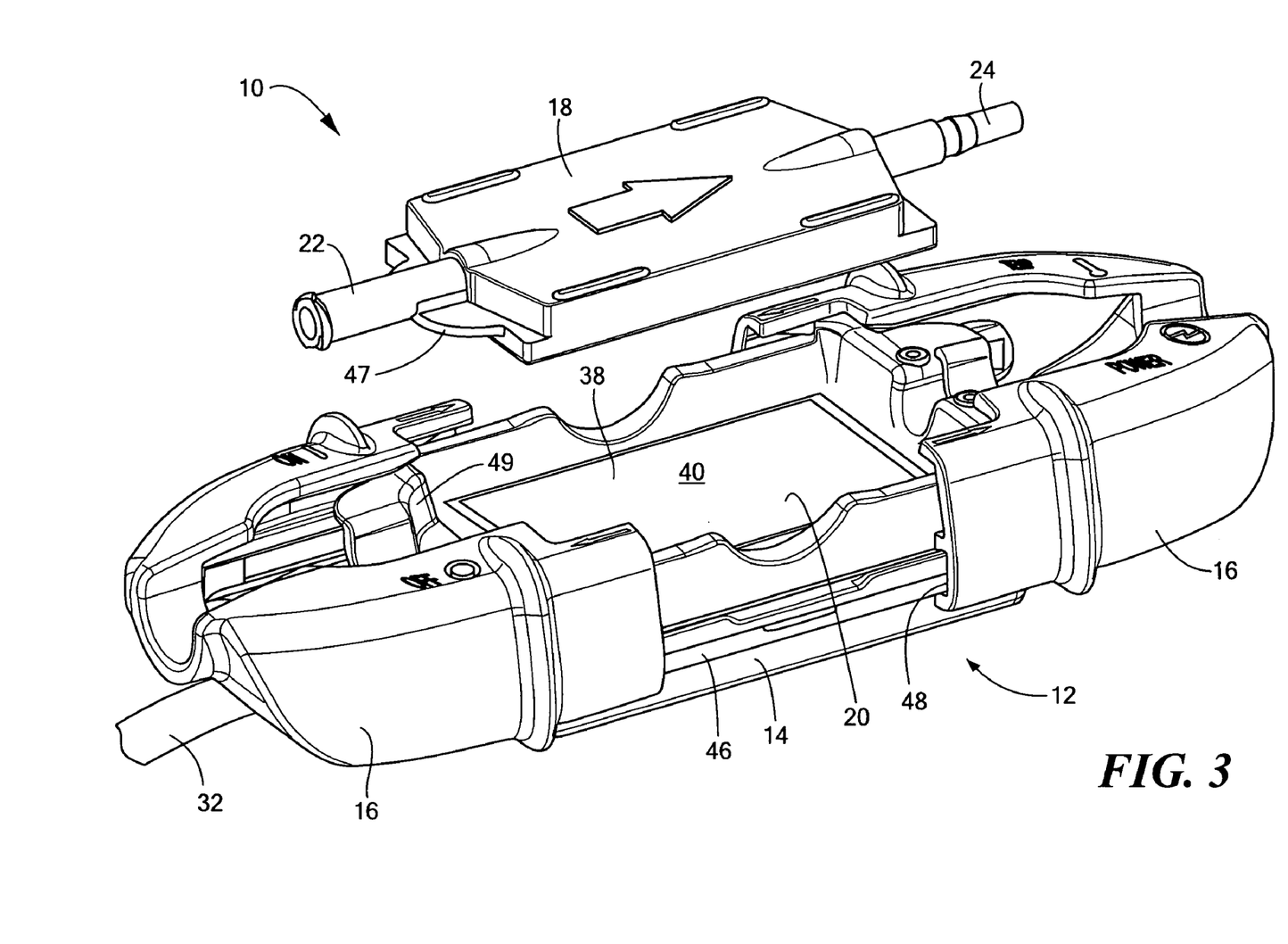
FIG. 3 is an isometric exploded view of the fluid warming device of FIG. 1 with the slidable covers in an open position and a disposable set removed.
Figure 4:
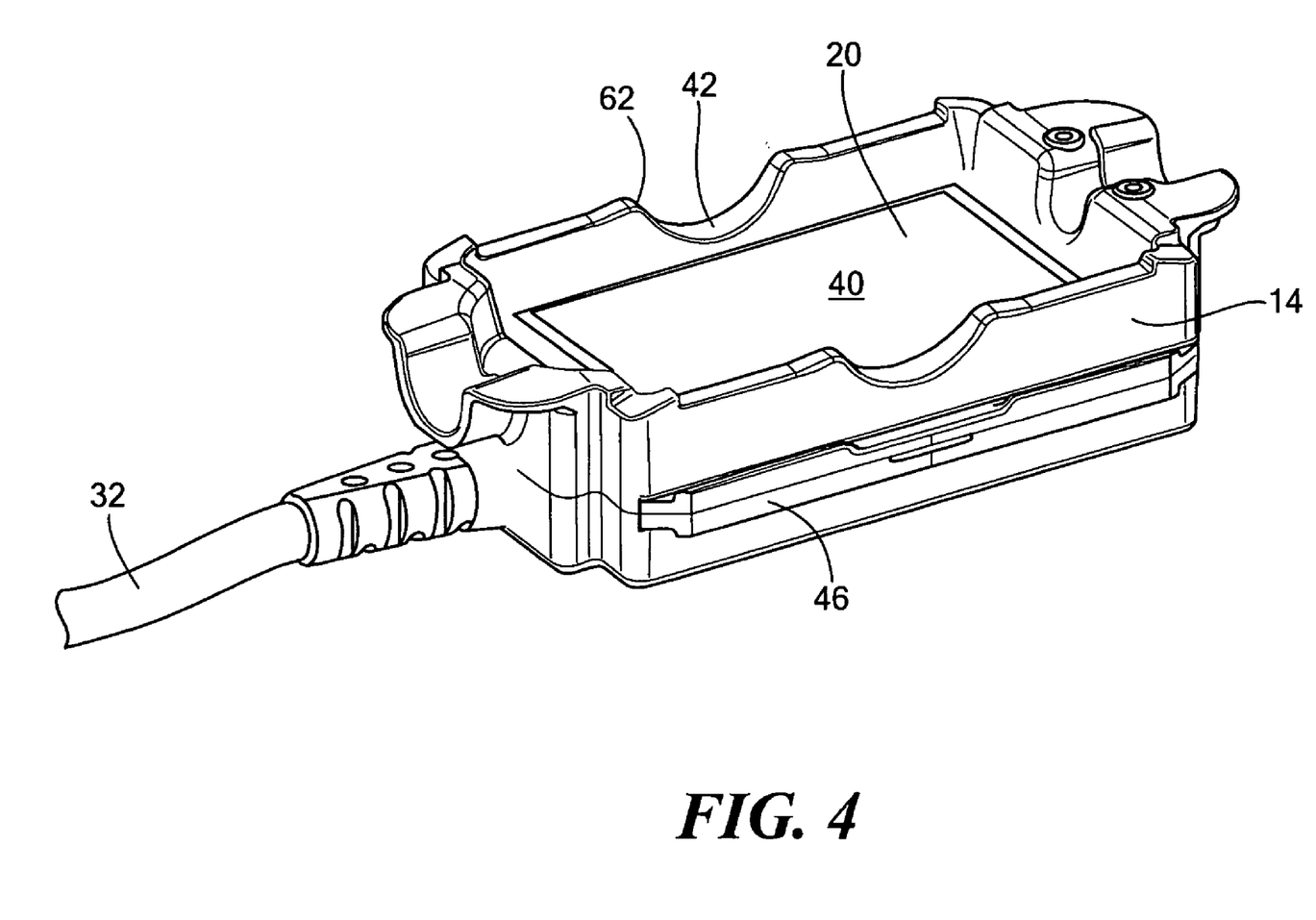
FIG. 4 is an isometric view of a main body of the housing of the device of FIG. 1 with the slidable covers fully removed.
Figure 5:
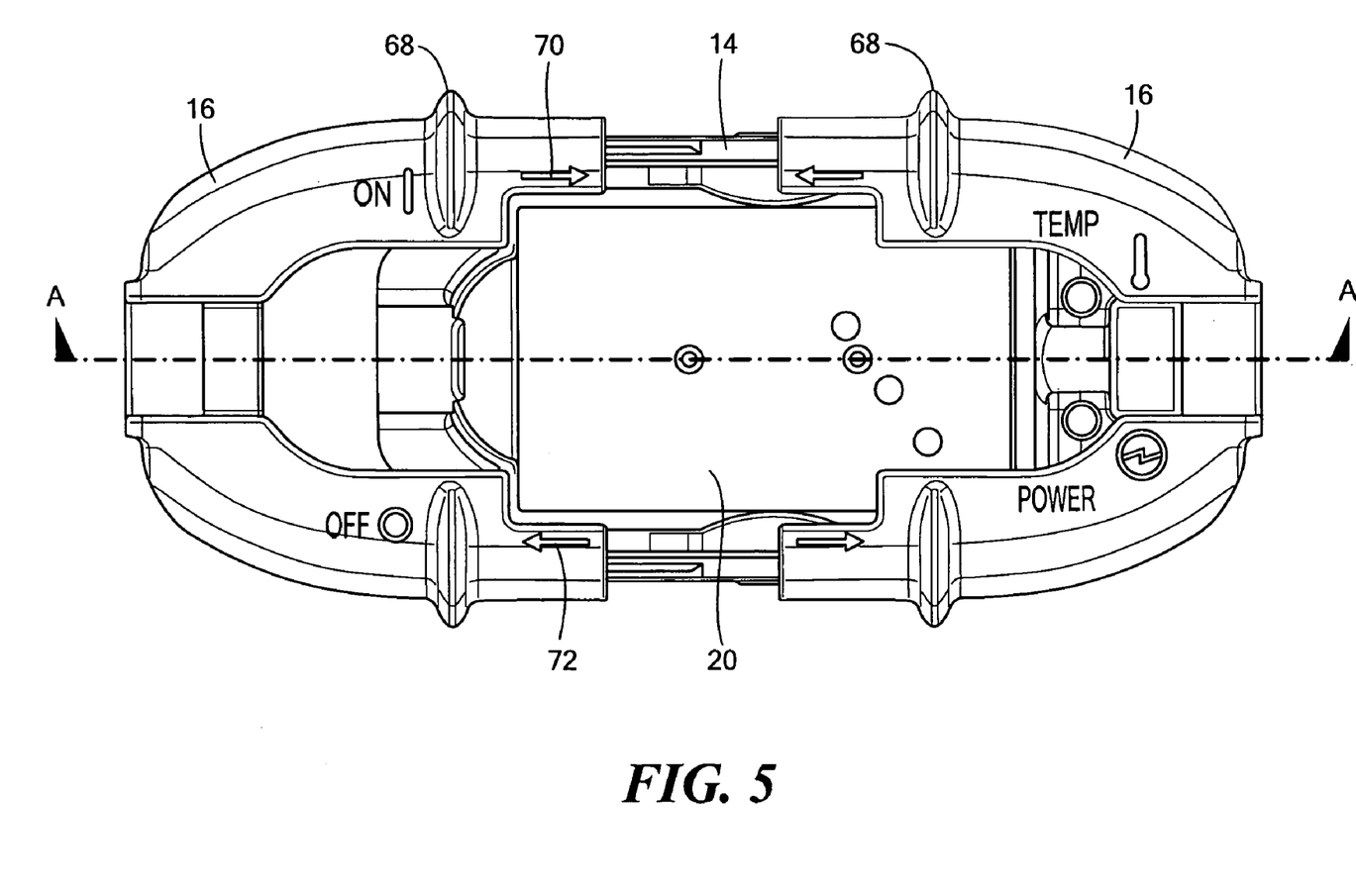
FIG. 5 is a plan view of the device of FIG. 2.
Figure 6:
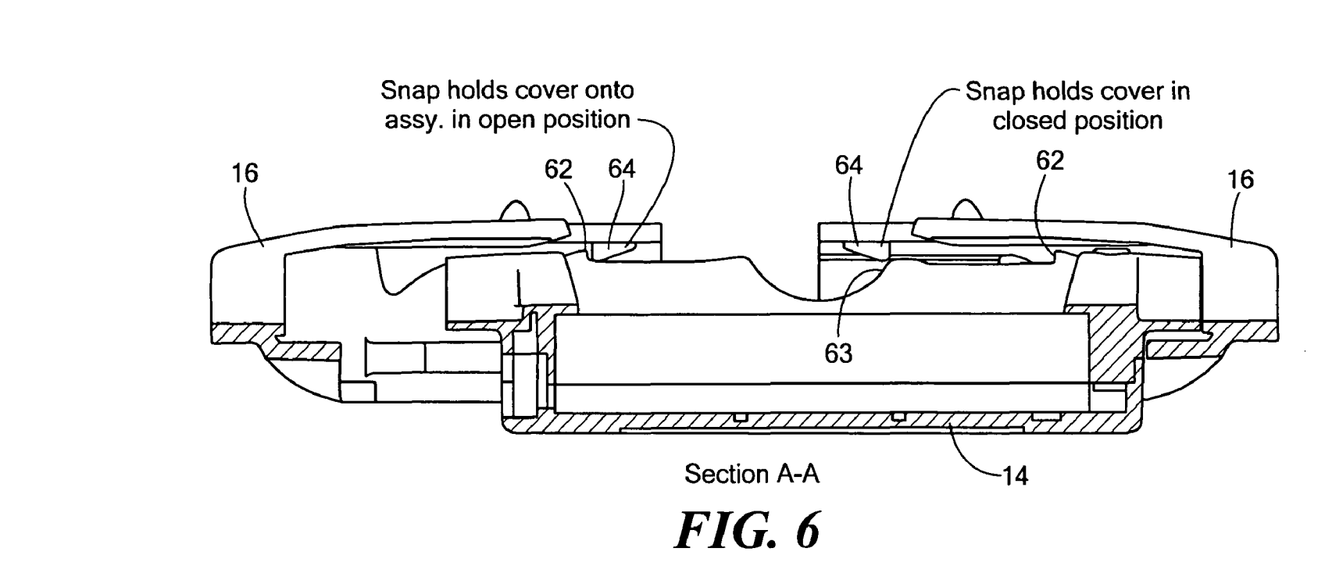
FIG. 6 is a cross sectional view taken along line A-A of FIG. 5.

Any suitable latching or retaining mechanism can be provided to retain the covers in the desired positions relative to the main body. For example, as shown in FIGS. 5 and 6, recessed surfaces 62 are provided on the main body 14 that latch with corresponding tabs 64 on the covers in the open position, preventing the covers from readily coming off the main body. Also, the tabs 64 abut surfaces 63 to hold the covers in the closed position. Finger grips 68 are provided to aid in grasping the covers to push or pull them to the desired position. The closed (and power on) position can be indicated by arrows 70 and an adjacent "ON" marking on the covers. Similarly, the open (and power off) position can be indicated by arrows 72 and an adjacent "OFF" marking on the covers. The covers can be fully removed from the main body in any suitable manner, for example, by the insertion of a suitable tool, such as a screw driver or dime, to lift the tab 64 over the surfaces 62. Alternatively, a latching or retaining mechanism can be configured to release simply by the use of sufficient force. Removal of the covers allows the device to be readily cleaned. Alternatively, passageways in the interior surfaces of the covers and a water tight main body housing allow cold sterilization by dipping in a sterilization fluid without complete removal of the covers.

Figure 8:
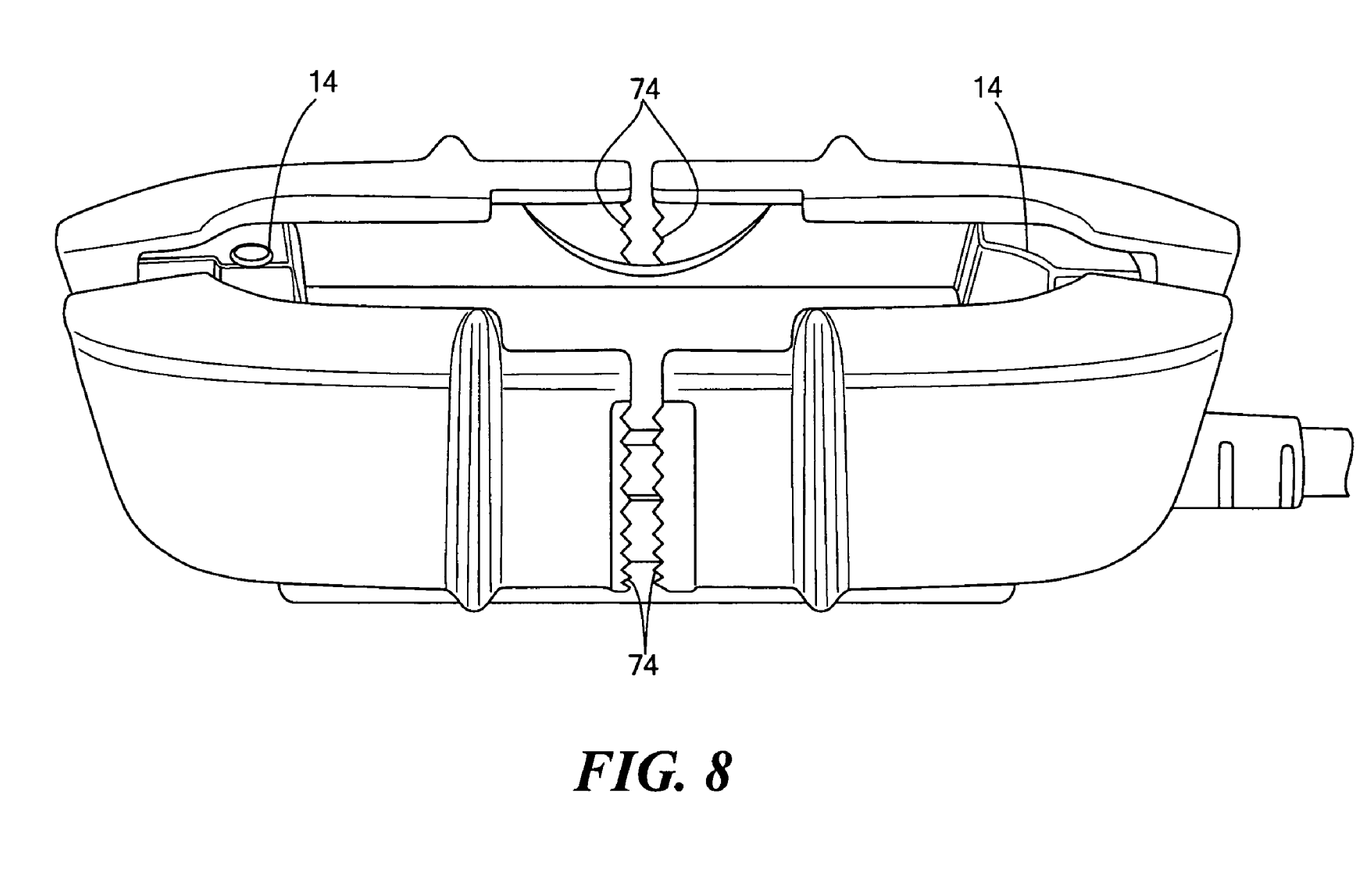
FIG. 8 is a side view of a further embodiment of a fluid warming device illustrating gripping faces on the slidable covers.

Referring to FIG. 8, the sliding covers 14 may include opposed faces 74 that include gripping teeth thereon to form gripping faces. The gripping faces can be used to grip hospital clothing or bedding and hold the warmer in place to reduce stress on the IV line when the covers are fully closed.

In another aspect of the present invention, power to the heater can be increased or decreased to adjust the fluid temperature to ensure that the fluid is at an appropriate temperature when it reaches the patient. More particularly, some IV fluids that have been warmed are administered at very low flow rates. These fluids cool as they travel down the IV tubing to the patient. The greater the difference between ambient temperature and the fluid temperature, the greater the radiated heat losses from the IV tubing.

A suitable controller is provided to perform the calculations and communicate with the heater to make the desired adjustments. Heater power is determined by the difference between a target temperature (typically in the range of 39 to 41° C.), and the actual fluid temperature.

Figure 9:
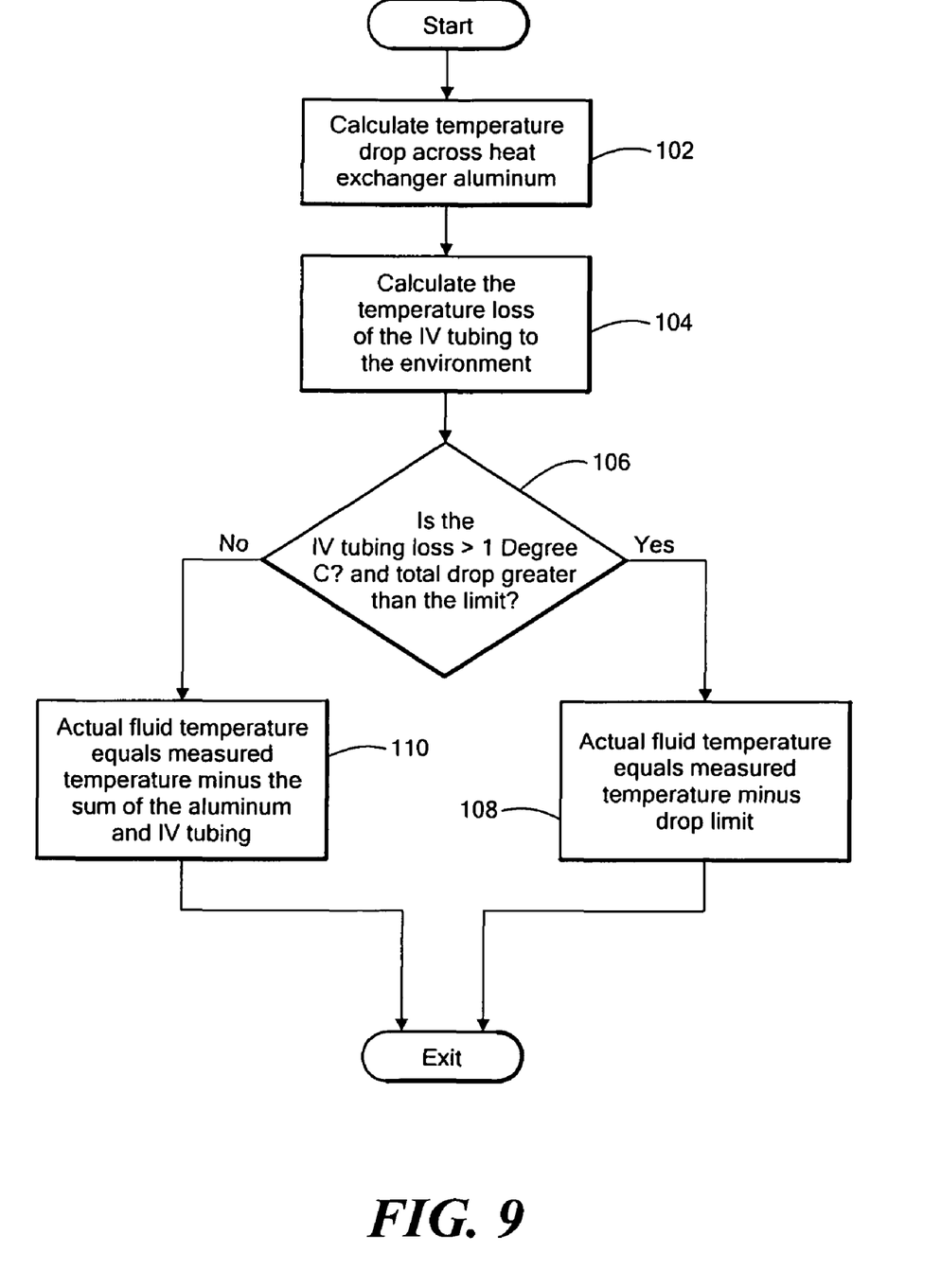
FIG. 9 is a flow chart illustrating a system for adjusting power to a heater of a fluid warming device to accommodate heat loss in an IV tubing at low flow rates.
Figure 10:
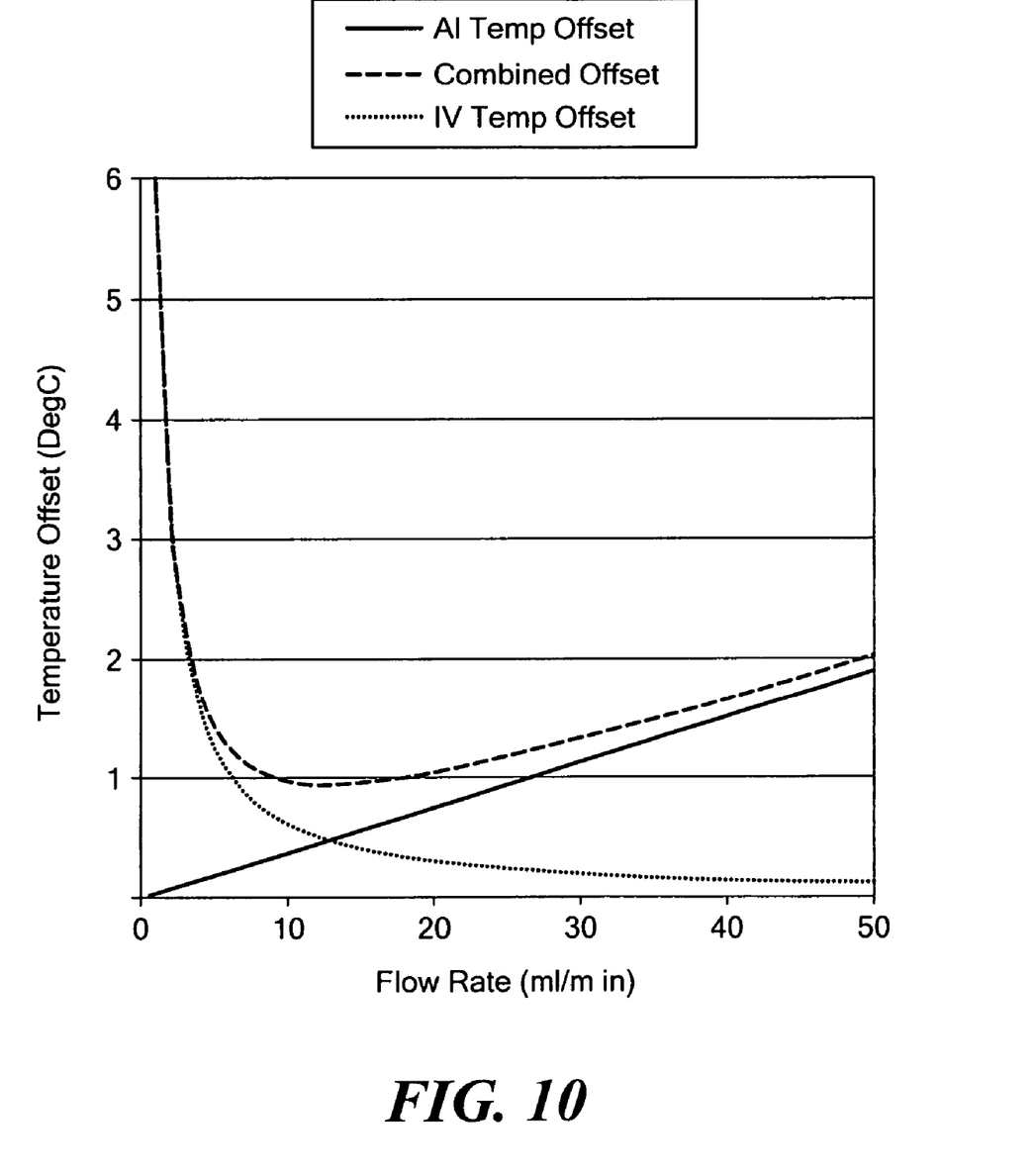
FIG. 10 is a graph illustrating heat loss across a disposable set heat exchange body and along a length of IV tubing and their combined heat losses.

Referring to FIG. 9, the temperature drop across the heat exchanger is calculated (step 102). This temperature drop is equal to the heater power divided by the thermal resistance of the heater assembly. The thermal resistance can be readily determined by one of skill in the art from the thickness, thermal conductivity and area of the materials between the heater and the fluid and stored as a constant.

Figure 11:
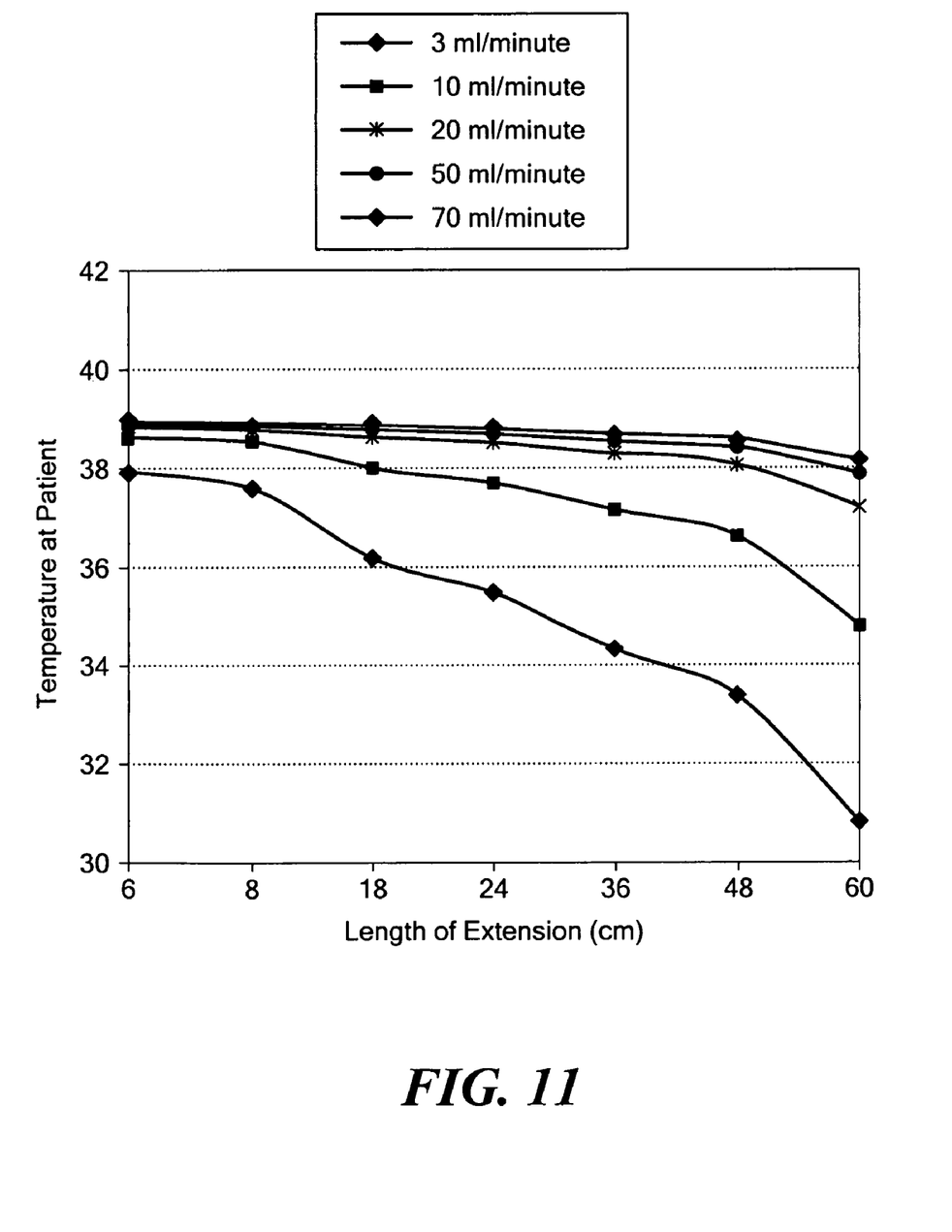
FIG. 11 is a graph illustrating temperature loss for various lengths of IV tubing and various flow rates.

Then, the controller calculates the temperature loss of the IV tubing to the environment (step 104). First, the difference between the fluid target temperature and the ambient temperature is determined. The temperature loss is equal to this temperature difference multiplied by the radiation loss and divided by the heater power. The ambient temperature is measured by a suitable sensor located within the warming device in close contact with the housing, which is very close to ambient temperature. The radiation loss is a constant that is derived from experimentation with various lengths of the IV tubing and various flow rates. See FIG. 11.

Next, at step 106, the controller determines if the IV tubing loss is greater than 1° C. Also at step 106, the controller also determines if the total drop along the IV tubing and across the heat exchanger is greater than a drop limit. The drop limit is the maximum temperature that the fluid can be artificially raised so that the allowable surface temperature on the heat exchanger is not exceeded, for example, no greater than 3° C. from the desired target temperature. If the answer at step 106 is Yes, the actual fluid temperature is calculated at step 108 as the measured fluid output temperature minus the drop limit. If the answer at step 106 is No, the actual fluid temperature is calculated at step 110 as the fluid output temperature in the IV tubing drop minus the IV tubing drop (from step 102) minus the heat exchanger drop (from step 104). Using the calculated value of the actual temperature, heater power is adjusted appropriately.

In this manner, heat loss along the IV tubing can be more efficiently controlled The system allows the fluid warming device to be located a bit farther from the infusion site and still deliver normothermic fluid.

The invention is not to be limited by what has been particularly shown and described, except as indicated by the appended claims.

What is claimed is:

1. A fluid warming device comprising:
   a housing comprising a main body and a pair of covers, the covers axially slidable on the main body, and a heat exchange body receiving compartment in the main body;
   a heater assembly disposed within the main body; and
   a heat exchange body removably disposable in the compartment of the main body in contact with a heat conducting surface of the heater assembly, the heat exchange body comprising a fluid input port, a fluid output port, and a fluid flow path from the fluid input port to the fluid output port, wherein the fluid input port is connectable to a first fluid line to receive a fluid and the fluid output port is connectable to a second fluid line to deliver the fluid;
   wherein the covers are slidable axially on the main body to a closed position in which the covers press the heat exchanger into heat exchange communication with the heater assembly.

2. The fluid warming device of claim 1, wherein the covers contact edges of the heat exchange body in the closed position and leave a mid portion of the heat exchange body visible.

3. The fluid warming device of claim 1, wherein the covers are slidable to an open position from which the heat exchange body can be removed from or inserted into the compartment in the main body.

4. The fluid warming device of claim 3, wherein the heat exchange body can be removed from or inserted into the compartment while attached to IV tubing.

5. The fluid warming device of claim 1, wherein the covers are retained in the closed position by frictional engagement with the heat exchange body.

6. The fluid warming device of claim 1, wherein the covers are slidable to a half closed position in which the covers still retain the heat exchange body within the compartment in the main body.

7. The fluid warming device of claim 1, wherein the covers include a switch to activate power to the heater assembly when the covers are in the closed position.

8. The fluid warming device of claim 1, wherein the heat exchange body includes visible indicators thereon, and the covers do not block the visible indicators when in the closed position.

9. The fluid warming device of claim 1, wherein the covers are slidable on longitudinal tracks on the main body of the housing.

10. The fluid warming device of claim 1, wherein fluid flowing through the heat exchange body is visible.

11. The fluid warming device of claim 1, wherein the covers are slidable in opposite directions between a fully closed position and an open position.

12. The fluid warming device of claim 1, wherein the covers are fully removable from the main body.

13. The fluid warming device of claim 1, wherein the covers are retained on the main body by a retaining mechanism.

14. The fluid warming device of claim 13, wherein the retaining mechanism comprises complementary latching surfaces on the covers and the main body.

15. The fluid warming device of claim 1, wherein the first and second fluid lines are each IV tubing.

16. A fluid warming device comprising:
   a housing comprising a main body and having a heat exchange body receiving compartment and a pair of covers axially slidable on the main body;
   a heater assembly disposed within the main body; and
   a heat exchange body removably disposable in the compartment of the main body in contact with a heat conducting surface of the heater assembly and configured to be coupled to intravenous tubing via an input port and an output port of the heat exchange body;
   wherein the covers press the heat exchanger into heat exchange communication with the heater assembly when in a closed position.

* * * * *